US012582563B2

(12) United States Patent
Umebayashi

(10) Patent No.: US 12,582,563 B2
(45) Date of Patent: Mar. 24, 2026

(54) RECLOSABLE UNDERWEAR-TYPE DISPOSABLE ARTICLE FOR WEARING AND MANUFACTURING METHOD THEREFOR

(71) Applicant: ZUIKO CORPORATION, Osaka (JP)

(72) Inventor: Toyoshi Umebayashi, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 631 days.

(21) Appl. No.: 17/917,960

(22) PCT Filed: Apr. 20, 2021

(86) PCT No.: PCT/JP2021/016007
§ 371 (c)(1),
(2) Date: Oct. 10, 2022

(87) PCT Pub. No.: WO2021/220878
PCT Pub. Date: Nov. 4, 2021

(65) Prior Publication Data
US 2023/0127980 A1 Apr. 27, 2023

(30) Foreign Application Priority Data

Apr. 29, 2020 (JP) ................................. 2020-079873

(51) Int. Cl.
*A61F 13/15* (2006.01)
*A61F 13/496* (2006.01)
(Continued)

(52) U.S. Cl.
CPC ............ *A61F 13/496* (2013.01); *A61F 13/62* (2013.01); *G06F 13/20* (2013.01); *G06F 13/28* (2013.01); *G06F 18/2148* (2023.01)

(58) Field of Classification Search
CPC ........ A61F 13/496; A61F 13/62; A61F 13/49; A61F 13/49004; A61F 13/49007;
(Continued)

(56) References Cited

U.S. PATENT DOCUMENTS 7,393,429 B2 7/2008 Tachibana
2002/0123730 A1* 9/2002 Popp ..................... A61F 13/622
604/385.03
(Continued)

FOREIGN PATENT DOCUMENTS

JP 4574548 B2 11/2010
JP 2014-226144 A 12/2014
(Continued)

OTHER PUBLICATIONS

International Search Report for corresponding Application No. PCT/JP2021/016007, mailed Jul. 13, 2021.

*Primary Examiner* — Jacqueline F Stephens
(74) *Attorney, Agent, or Firm* — Renner, Otto, Boisselle & Sklar, LLP

(57) ABSTRACT

While in an unused folded state of a worn article, flaps are engaged with second touch fasteners in a protruding end portion via first touch fasteners, and the flaps are folded so that the protruding end portion comes closer to a proximal end portion, and while in a worn state in which the worn article is used, the flaps can be developed so that the first touch fasteners of the protruding end portion can oppose and engage with the second touch fasteners.

15 Claims, 12 Drawing Sheets

(51) Int. Cl.

| | |
|---|---|
| *A61F 13/62* | (2006.01) |
| *G06F 13/20* | (2006.01) |
| *G06F 13/28* | (2006.01) |
| *G06F 18/214* | (2023.01) |

(58) Field of Classification Search

CPC ............ A61F 13/4906; A61F 13/49601; A61F
13/5644; A61F 13/72; A61F 2013/5666;
A61F 2013/586; G06F 13/20; G06F
13/28; G06F 18/2148; G06F 18/2193;
G06F 2213/28; G07C 5/008; G07C
5/0841

See application file for complete search history.

(56) References Cited

U.S. PATENT DOCUMENTS

| | | | |
|---|---|---|---|
| 2003/0088223 A1 * | 5/2003 | Vogt .................. | A61F 13/15756 604/385.01 |
| 2006/0052763 A1 * | 3/2006 | Tachibana ......... | A61F 13/15699 604/395 |
| 2014/0115757 A1 | 5/2014 | Umebayashi | |

FOREIGN PATENT DOCUMENTS

| | | |
|---|---|---|
| JP | 6013331 B2 | 10/2016 |
| WO | 2012/176386 A1 | 12/2012 |

* cited by examiner (a)

(b)

(c)

(d)

(e)

(f)

RECLOSABLE UNDERWEAR-TYPE DISPOSABLE ARTICLE FOR WEARING AND MANUFACTURING METHOD THEREFOR

TECHNICAL FIELD

The present invention relates to a reclosable pants-type disposable worn article and a method for manufacturing the same.

BACKGROUND ART

With a worn article of this type, the front panel is separated or separable into left and right parts, and these front panels are engaged with the crotch member with touch fasteners therebetween (the first patent document and the second patent document below). With such a reclosable worn article, it is possible to adjust the around-torso sizes by disengaging the touch fasteners of the left and right front panels.

CITATION LIST

Patent Document

[FIRST PATENT DOCUMENT] JP 4,574,548 B
[SECOND PATENT DOCUMENT] JP 6,013,331 B

SUMMARY OF INVENTION

With the conventional techniques, however, when adjusting the around-torso size to a smaller size, the touch fastener of one front panel is engaged with the outer surface of the other front panel. The outer surface of the other front panel is made of non-woven fabric, not a fastener member, and therefore a sufficient engagement force cannot be obtained. In order to realize a large engagement force, there is a need to change the outer surface of the front panel to a fluffy material such as a loop material.

Thus, it is an object of the present invention is to provide a reclosable pants-type disposable worn article and a method for manufacturing the same, with which a sufficient engagement force can be obtained from the touch fastener after size adjustment even if the material of the front panel is made of an ordinary non-woven fabric.

A worn article of the present invention is a reclosable pants-type disposable worn article N including:

a front panel 1 and a back panel 2 covering a torso of a wearer;

a crotch member 3 covering crotch of the wearer and connecting between the front panel 1 and the back panel 2;

a separation portion 10 formed on the front panel 1, thereby making the front panel 1 separated or separable into left and right parts;

a pair of flaps 4 provided in an area of the crotch member 3 that opposes the front panel 1 and extending in a left-right direction X from a proximal end portion 41 to a protruding end portion 42;

a pair of left and right first touch fasteners F provided on a non-skin-contact side 4B of at least the protruding end portion 42 of the pair of flaps 4; and a pair of second touch fasteners M provided on a skin-contact side 1F of the front panel 1 and engaging with the pair of first touch fasteners F, thereby allowing the front panel 1 to be re-fastened to the crotch member 3, wherein:

the pair of second touch fasteners M are provided both on a left side and a right side of the separation portion 10 with the separation portion 10 interposed therebetween;

while in an unused folded state of the worn article, the flaps 4 are engaged with the second touch fasteners M in the protruding end portion 42 via the first touch fasteners F, and the flaps 4 are folded so that the protruding end portion 42 comes closer to the proximal end portion 41; and while in a worn state in which the worn article is used, the flaps 4 can be developed so that the first touch fasteners F of the protruding end portion 42 can oppose and engage with the second touch fasteners M.

A manufacturing method of the present invention is a method for manufacturing a reclosable pants-type disposable worn article N, wherein the worn article includes:

a front panel 1 and a back panel 2 covering a torso of a wearer;

a crotch member 3 covering crotch of the wearer and connecting between the front panel 1 and the back panel 2;

a separation portion 10 formed on the front panel 1, thereby making the front panel 1 separated or separable into left and right parts;

a pair of flaps 4 provided in an area of the crotch member 3 that opposes the front panel 1 and extending in a left-right direction X from a proximal end portion 41 to a protruding end portion 42;

a pair of left and right first touch fasteners F provided on a non-skin-contact side 4B of at least the protruding end portion 42 of the pair of flaps 4; and a pair of second touch fasteners M provided on a skin-contact side 1F of the front panel 1 and engaging with the pair of first touch fasteners F, thereby allowing the front panel 1 to be re-fastened to the crotch member 3, wherein:

the pair of second touch fasteners M are provided both on a left side and a right side of the separation portion 10 with the separation portion 10 interposed therebetween; and the method for manufacturing a worn article includes:

a step of conveying a rear continuous body W2 to be the back panel 2 in such a manner that an around-torso direction is a conveyance direction;

a step of conveying a precursor member to be the front panel 1 in such a manner that an around-torso direction is a conveyance direction;

a bridging step of providing the crotch member 3 so as to bridge between the rear continuous body W2 and the precursor member being conveyed;

a step of, prior to the bridging step, folding a flap member W4 to be the flaps 4 so that the protruding end portion 42 of the pair of flaps 4 comes closer to the proximal end portion 41 and so that the first touch fasteners F are exposed in the protruding end portion 42; and an engagement step of, while the first touch fasteners F is exposed, engaging a pair of second touch fasteners M arranged on the precursor member with the first touch fasteners F.

According to the present invention, it is possible to adjust the around-torso size by changing the position of engagement of the second touch fastener relative to the first touch fastener. Moreover, an ordinary non-woven fabric can be used as the material of the front panel, and there is no need to use a loop material.

BRIEF DESCRIPTION OF THE DRAWINGS

FIG. 1A and FIG. 1B relate to one embodiment of a worn article of the present invention, wherein FIG. 1A is a plan view of an unused worn article and FIG. 1B is a front view thereof.

FIG. 3B is a plan view of the worn article being used. Note that while FIG. 3A is the same view as FIG. 1A and FIG. 3B is the same view as FIG. 4A, the views are arranged one on top of the other so that it is easy to see differences between when unused and when being used.

FIG. 10A and FIG. 10B show a part of a front panel according to another embodiment of the worn article of the present invention, wherein FIG. 10A is a front view of a front panel and a male touch fastener as viewed from the skin-contact side and FIG. 10B is a bottom view thereof.

In FIG. 1A to FIG. 5B, the welded portion (side seal portion) between the front panel and the back panel is shown in gray. In FIG. 8 and FIG. 9, the female touch fastener is shown in gray. In FIG. 4B and FIG. 5B, the female touch fastener is shown in a geometric pattern, and in FIG. 4B, FIG. 5B and FIG. 10A, the male touch fastener is shown in a dot pattern.

DESCRIPTION OF EMBODIMENTS

Figure 1A:
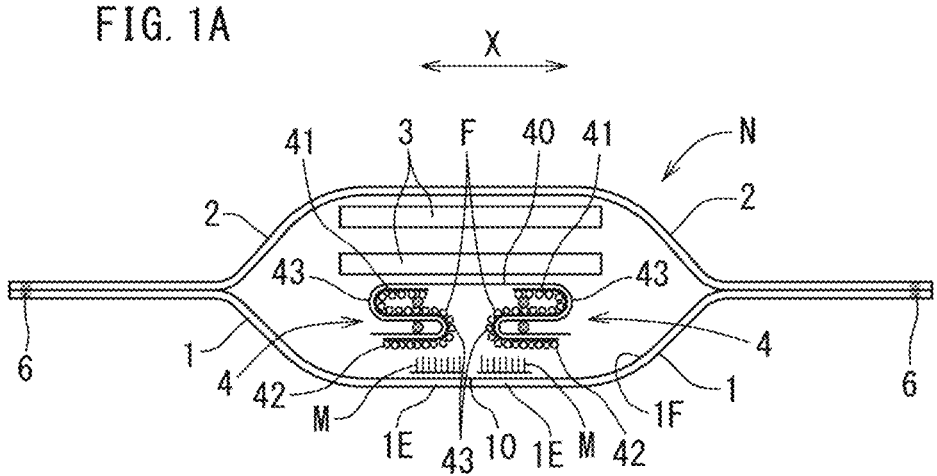

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

One embodiment of the present invention will now be described with reference to the drawings.

Figure 1B:
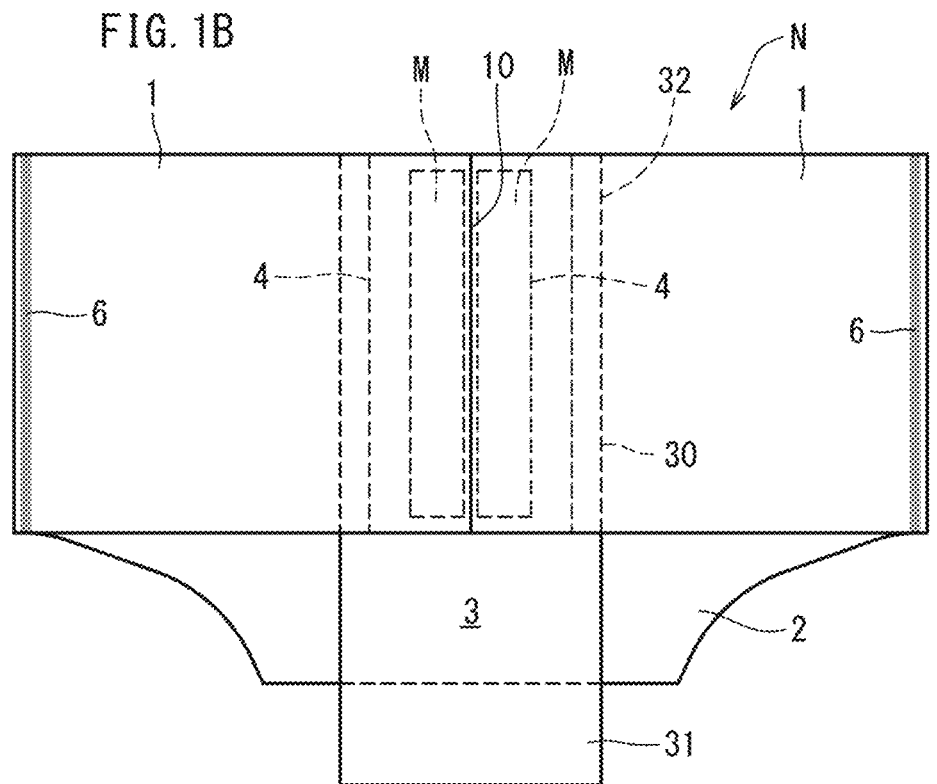

FIG. 1A and FIG. 1B show a pants-type article in an unused state. As shown in these figures, a worn article N includes a front panel 1, a back panel 2 and a crotch member 3.

Figure 2:
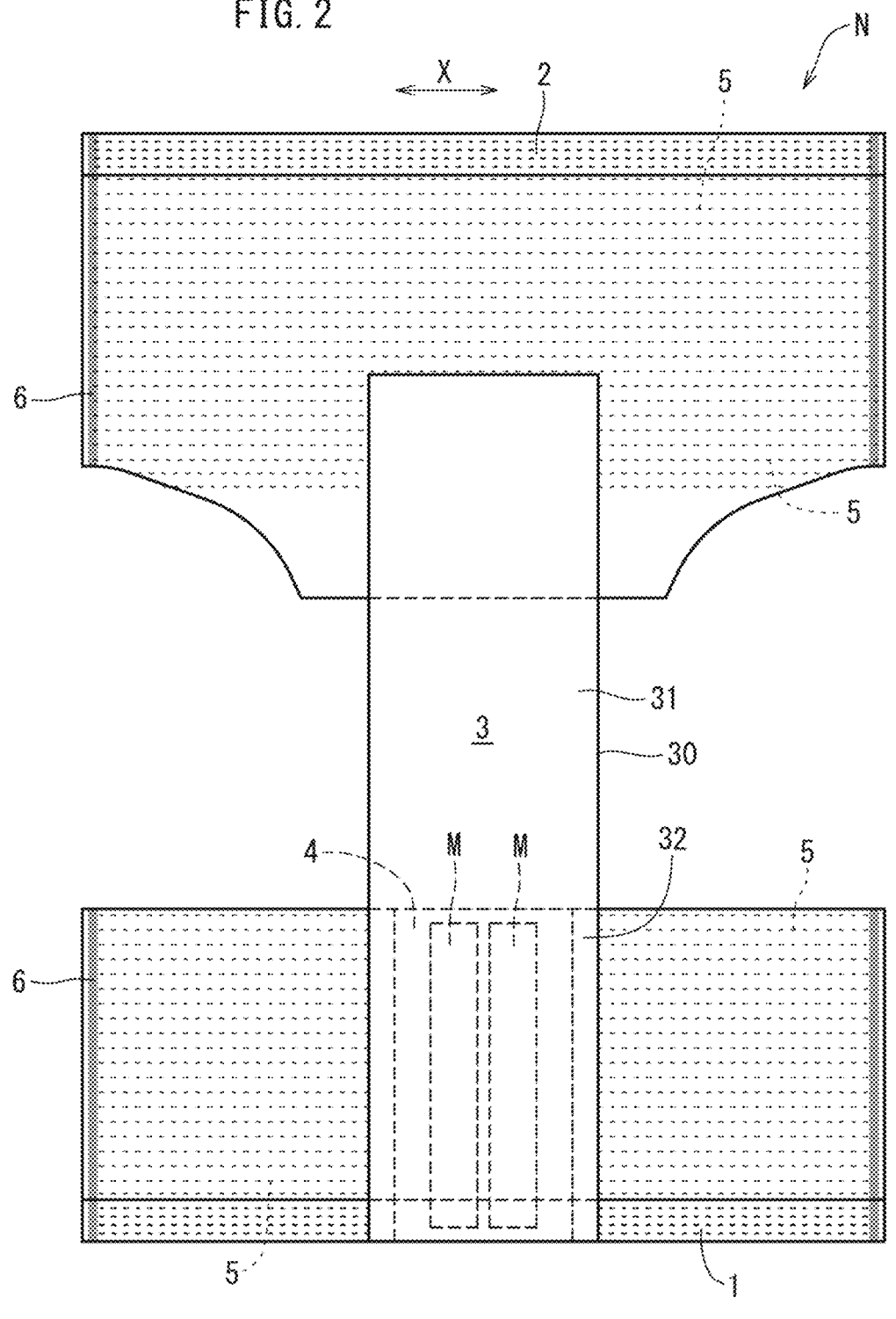
FIG. 2 is a developed view of the worn article.
Figure 4A:
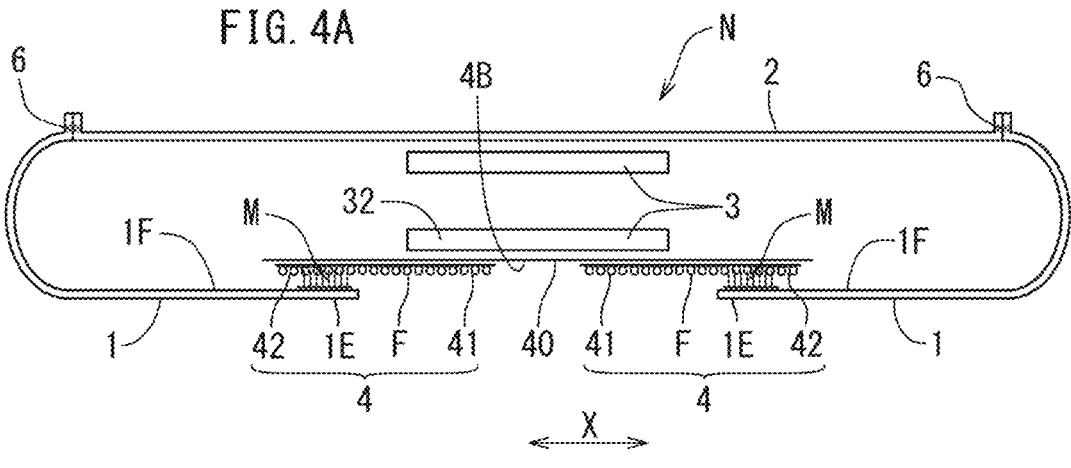
FIG. 4A is a plan view of the same when being used.
Figure 4B:
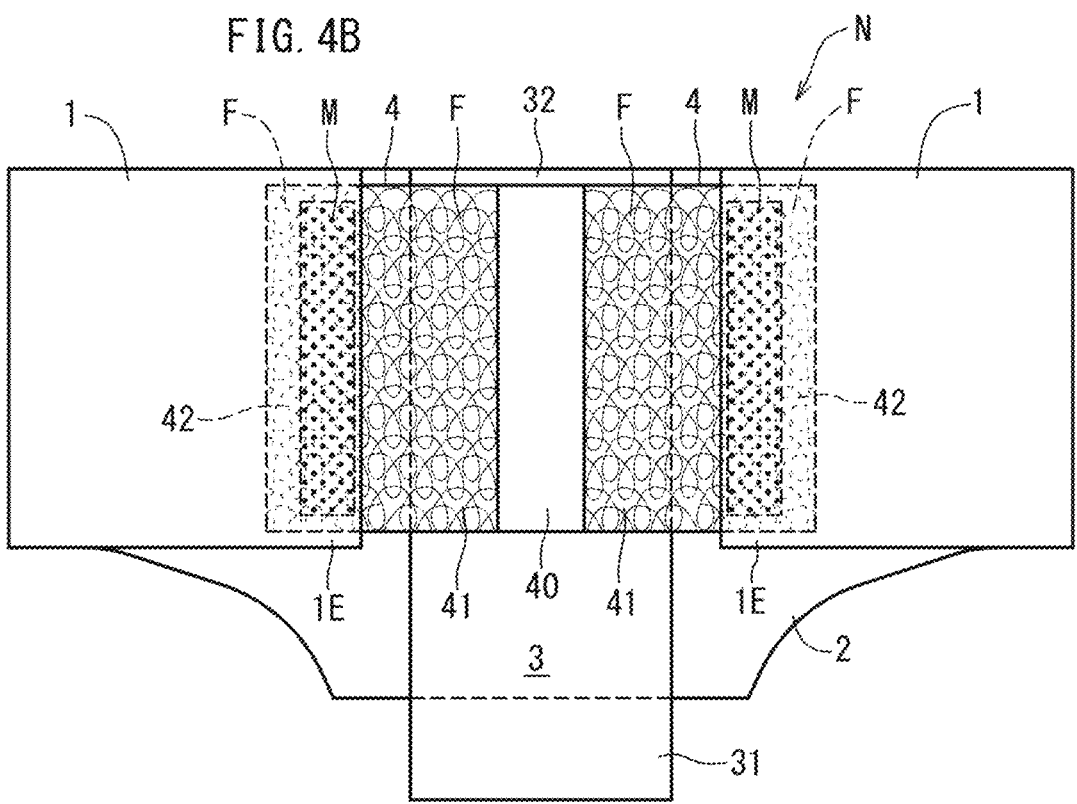
FIG. 4B is a front view thereof.

In a used state shown in FIG. 4A and FIG. 4B, the front panel 1 and the back panel 2 cover the torso of the wearer. On the other hand, the crotch member 3 covers the crotch of the wearer, and connects between the front panel 1 and the back panel 2 as shown in FIG. 2. The crotch member 3 includes a longitudinal portion 30 that extends from a crotch portion 31 covering the crotch to a front torso portion 32 covering the front torso of the wearer.

As shown in FIG. 2, the front panel 1 and the back panel 2 may be formed with a large number of elastic members 5, extending in the around-torso direction, i.e., the left-right direction X, sandwiched between two sheets of non-woven fabric. On the other hand, the crotch member 3 may have a structure with which an absorbent body (not shown) can be attached/detached to/from the crotch member 3.

As shown in gray in FIG. 1B, the front panel 1 and the back panel 2 of FIG. 1A are welded to each other along a side seal portion 6 at the side edge so as to be continuous with each other. On the other hand, the front panel 1 includes a separation portion 10. With the separation portion 10, the front panel 1 is separated or separable into left and right parts. In the case of the present embodiment, the front panel 1 is cut along the longitudinal direction (direction orthogonal to the left-right direction) at the center in the left-right direction X.

The separation portion 10 may be formed by perforations or thermally-deteriorated fragile portions so that the front panel 1 is continuous in the left-right direction when unused and is separable by being torn when in use. The separation portion 10 may be separated in the left-right direction in advance when unused.

As shown in FIG. 4A and FIG. 4B, a pair of flaps 4, 4 are provided in an area of the crotch member 3 that opposes the front panel 1. In the present embodiment, the pair of flaps 4, 4 include a flap body 40 separate from the crotch member 3, the flap body 40 being attached to the front torso portion 32 of the longitudinal portion 30. Note that the flaps 4, 4 may be formed integral with the crotch member 3.

The left and right flaps 4 of FIG. 4A each include a proximal end portion 41 attached to the front torso portion 32 of the longitudinal portion 30 and a protruding end portion 42 protruding in the left-right direction X from the front torso portion 32. A female touch fastener (an example of the first touch fastener) F is provided on the non-skin-contact side 4B extending from the proximal end portion 41 to the protruding end portion 42 of each flap.

On the other hand, a male touch fastener (an example of the second touch fastener) M is provided on the skin-contact side 1F of separation end portions 1E of the left and right front panels 1 of FIG. 4A. The male touch fasteners M engage with the female touch fasteners F. The pair of left and right separation end portions 1E, 1E are adjacent to each other with the separation portion 10 interposed therebetween.

In the present invention, "skin-contact side" refers to the side opposing the skin of the wearer, and "non-skin-contact side" refers to the side opposite to the skin-contact side.

Figure 3A:
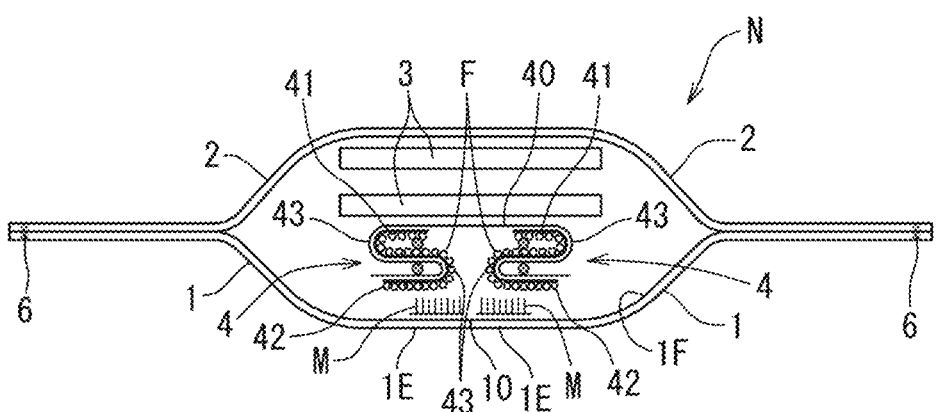
FIG. 3A is a plan view of the unused worn article.
Figure 3B:
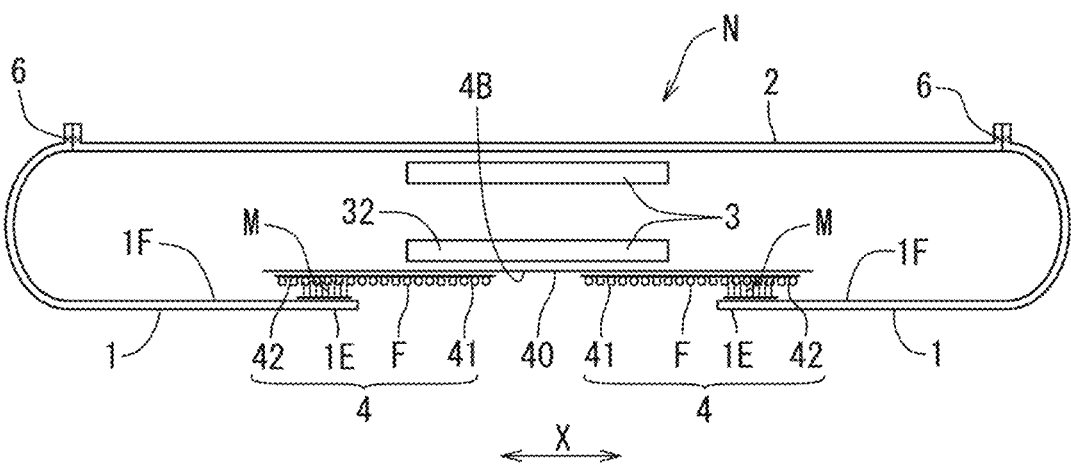
Figure 5A:
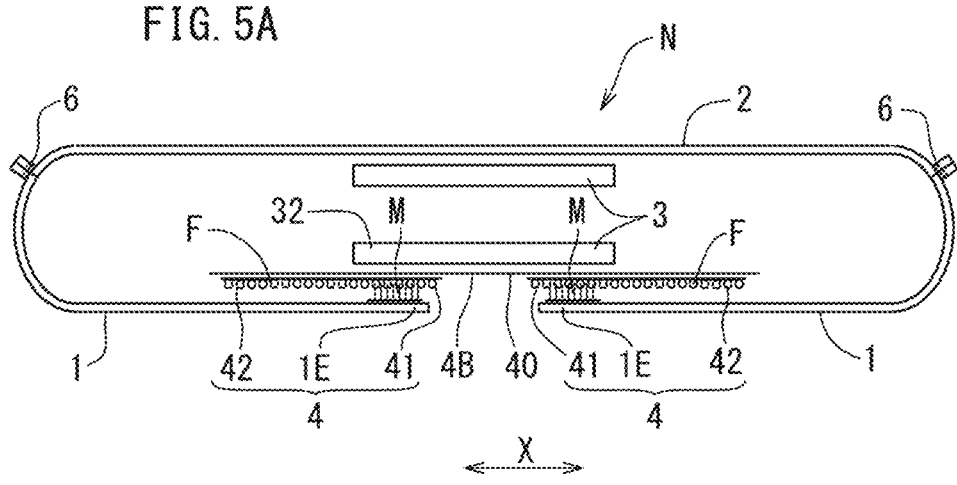
FIG. 5A is a plan view of the worn article where the around-torso size is reduced.

The male touch fasteners M of FIG. 1A are separated from each other with the separation portion 10 interposed therebetween, and engage/disengage with/from the female touch fasteners F so that the front panel 1 can be re-fastened to the crotch member 3 as shown in FIG. 5A and FIG. 3B. Note that the male touch fasteners M do not always need to be separated in advance as long as the male touch fasteners M are provided on both of the separation end portions 1E, 1E on the left side and the right side of the separation portion 10 with the separation portion 10 interposed therebetween.

As will be described below, the present worn article N is used as its form is changed from the unused folded state of FIG. 3A to the worn state of FIG. 3B.

In the unused folded state of FIG. 3A, the flaps 4 are folded so that the protruding end portions 42 thereof engage with the male touch fasteners M with the female touch fasteners F therebetween, and at least portions of the proximal end portions 41 thereof are hidden by at least portions of the protruding end portions 42. Note that it is only required that the protruding end portions 42 be folded so as to come closer to the proximal end portions 41. On the other hand, as shown in FIG. 4A, the flaps 4 are configured to be developed so that the female touch fasteners F of the protruding end portions 42 can oppose the male touch fasteners M and engage with the male touch fasteners M.

In the unused state of FIG. 3A, the flaps 4 may be folded in a Z-letter shape or S-letter shape with two folded portions 43, as in the case of this example. In this state, the male touch fasteners M engage with the female touch fasteners F of the protruding end portions 42.

Figure 5B:
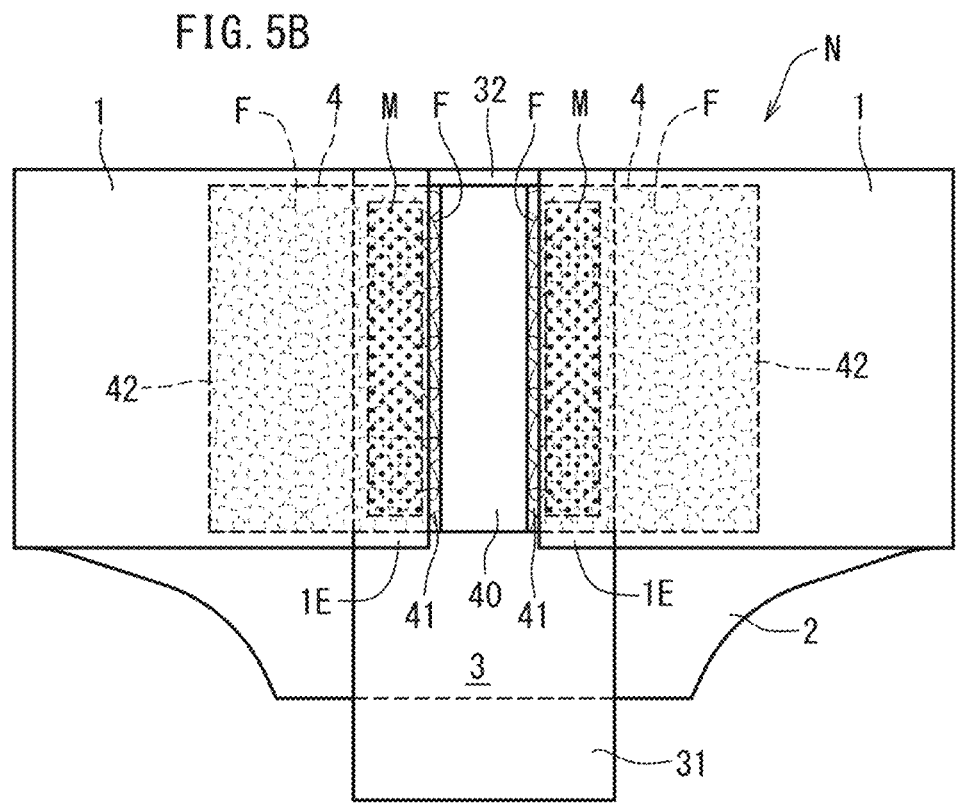
FIG. 5B is a front view thereof.

As shown in FIG. 3B, when being used by a wearer having a large waist size, each male touch fastener M engages with the female touch fastener F in the protruding end portion 42 of the flap 4. On the other hand, as shown in FIG. 5B and FIG. 5A, when being used by a wearer having a small waist size, each male touch fastener M engages with the female touch fastener F in the proximal end portion 41 of the flap 4.

Thus, with the worn article N of the present embodiment, the male touch fastener M engages with the female touch fastener F whether the waist size of the wearer is large or small. Therefore, it is possible to obtain a sufficient engagement force by touch fasteners after size adjustment.

Next, prior to the description of the overall manufacturing method for manufacturing the worn article N, a method for manufacturing the crotch member 3 of FIG. 7 and FIG. 8 will be described.

Figure 6:
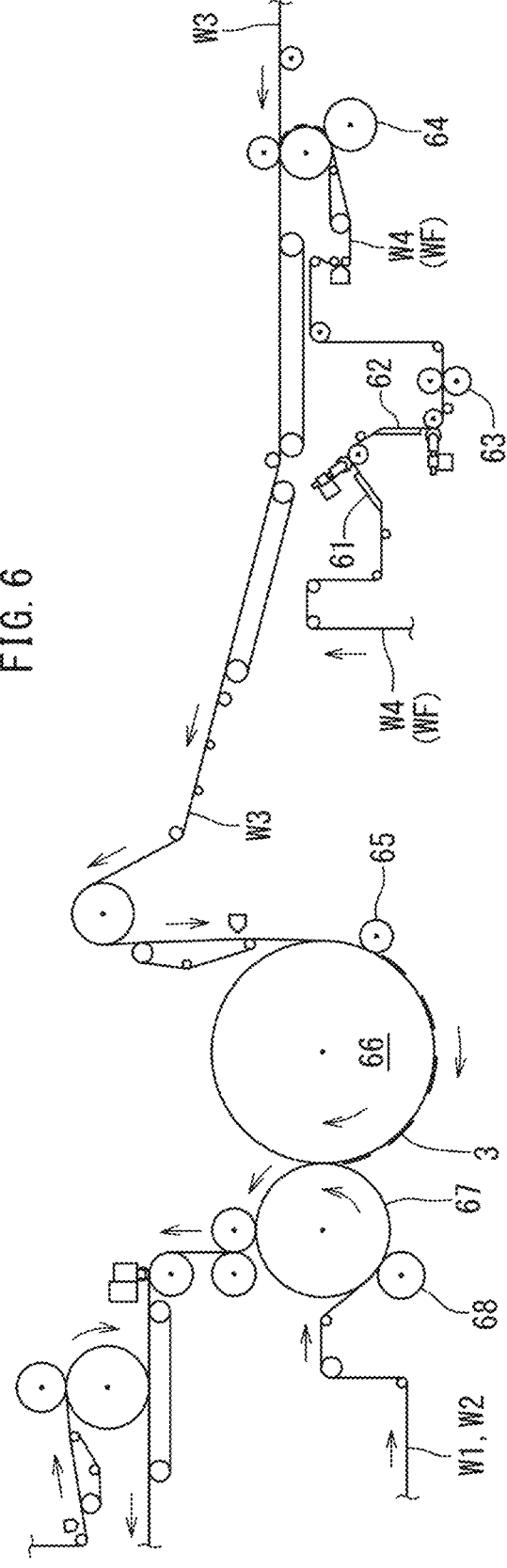
FIG. 6 is a layout diagram showing an example of an equipment for manufacturing a worn article.

Female touch fastener members WF and flap members W4, attached together, of FIG. 7(a) are supplied in the continuous direction to a first folder device 61 of FIG. 6. As shown in FIG. 7(b), the first folder device 61 folds the end portions of the female touch fastener members WF and the flap members W4 at the first folded portions 43 in such a direction that the flap members W4 face (oppose) each other. Then, as shown in FIG. 7(c), a second folder device 62 (FIG. 6) folds the female touch fastener members WF and the flap members W4 at the second folded portions 43 in such a direction that the female touch fastener members WF face (oppose) each other.

Thus, the flap member W4 to which the female touch fastener members WF are attached is folded in left-right symmetry so that one end portion is folded in a Z-letter shape and the other end portion in an inverted Z-letter shape. As shown in FIG. 8, these folding steps are performed while the female touch fastener member WF and the flap member W4 are a continuous body that is continuous in the conveyance direction.

That is, as shown in FIG. 7(c), in these folding steps, the flap members W4 to be the flaps 4 are folded so that the proximal end portions 41 of the pair of flaps 4 described above are hidden by the protruding end portions 42 and so that the female touch fasteners F are exposed in the protruding end portions 42. Thus, the female touch fastener members WF to be the female touch fasteners F are folded together with the flap members W4 to be the flap bodies 40.

After the folding, a tentative fastening step may be performed. In the tentative fastening step, a portion of the female touch fastener F of FIG. 7(d) may be welded by a welding roll 63 of FIG. 6 so that the proximal end portion 41 and the protruding end portion 42 are mildly attached together with a middle portion 45 therebetween at the tentative fastening portion 44.

Figure 8:
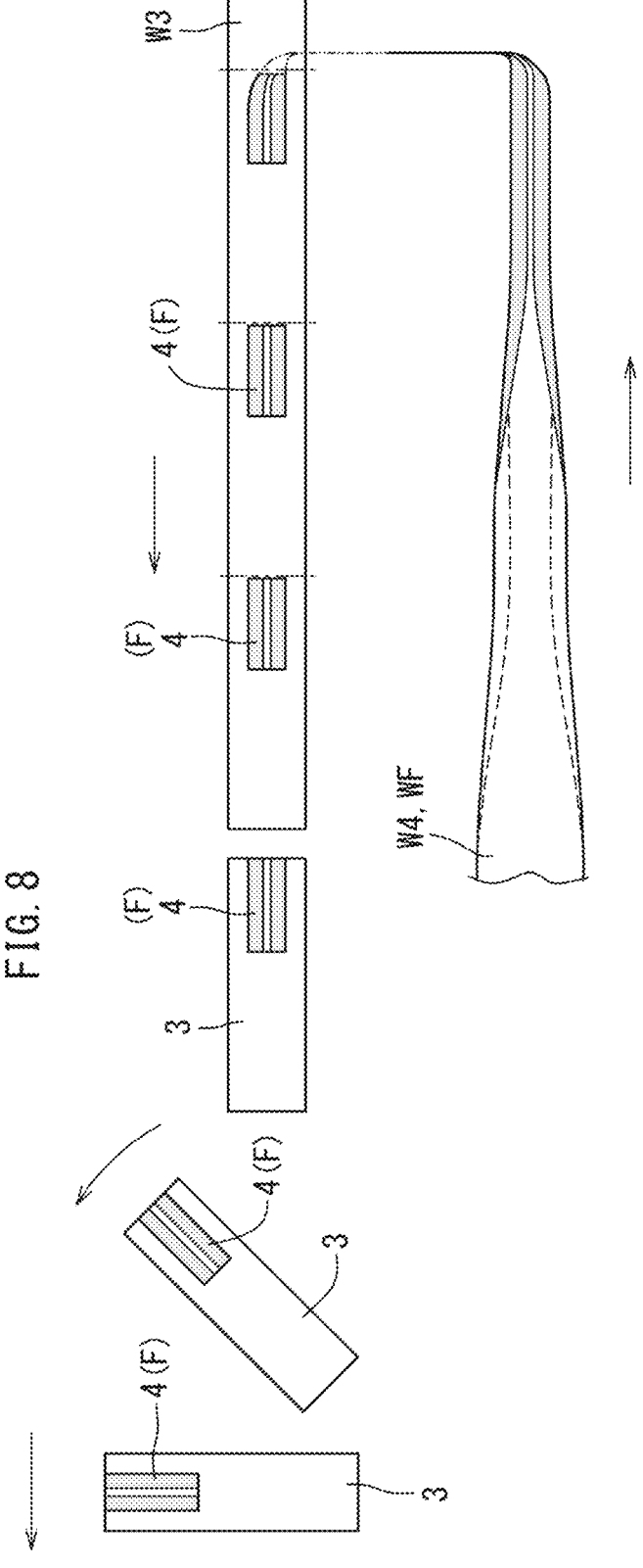
FIG. 8 is a plan view showing a method for manufacturing a crotch member.

After the tentative fastening step, the flap member W4 of FIG. 8 is severed by a cutter roll 64 of FIG. 6 into individual units of worn articles, which are then arranged on a crotch continuous body W3 to be the crotch member 3 of FIG. 8 by a cut-and-slip method well known in the art.

The crotch continuous body W3 of FIG. 6 is severed by a cutter 65 into individual units of crotch members 3, and the attitude of each crotch member 3 is changed by 90° by a re-pitch turn drum 66 as shown in FIG. 8. Thus, as shown in FIG. 7(e), the flaps 4, 4 in a folded state are bonded to the crotch member 3.

Next, the overall manufacturing method for manufacturing the worn article N will be described with reference to FIG. 6 and FIG. 9.

Figure 9:
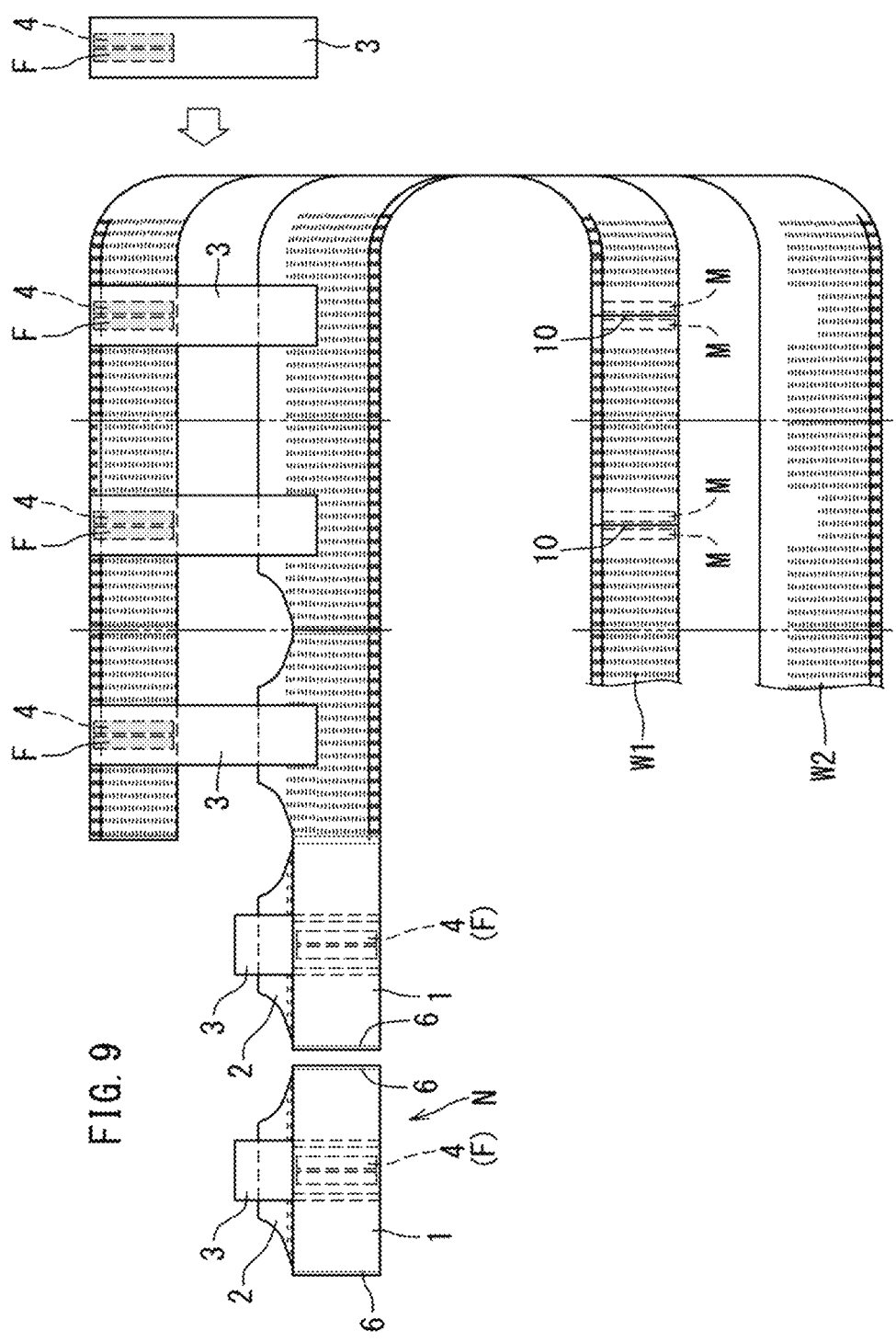
FIG. 9 is a plan view showing a method for manufacturing a worn article.

As shown in FIG. 9, a rear continuous body W2 to be the back panel 2 is conveyed in such a manner that the around-torso direction is the conveyance direction, and a front continuous body W1 to be the front panel 1 is conveyed in such a manner that the around-torso direction is the conveyance direction. These are conveyed in parallel to each other, and the crotch member 3 is provided so as to bridge between the rear continuous body W2 and the front continuous body W1 being conveyed. A pair of male touch fasteners M are bonded, for each unit of the worn article N, to the front continuous body W1 to be the front panel 1.

These steps are ordinary steps, and the bridging step is performed by the re-pitch turn drum 66 and a vacuum drum 67 of FIG. 6. In this bridging step, the crotch member 3 of FIG. 9 is provided so as to bridge between the front continuous body W1 and the rear continuous body W2 while the female touch fastener F (first touch fastener) of FIG. 7) is exposed and so that a pair of male touch fasteners M (second touch fasteners) arranged on the front continuous body W1 engage with the female touch fastener F.

Here, before the crotch member 3 is provided so as to bridge between the front continuous body W1 and the rear continuous body W2, a front portion cutter 68 being in contact with the vacuum drum 67 of FIG. 6 severs the front continuous body W1 as shown in FIG. 9 so as to form the separation portion 10 for each front panel 1. Thus, the crotch member 3 and the flap 4 are arranged on the front continuous body W1 with the separation portion 10 of FIG. 7(f) formed therein.

In this process, the pair of crotch members 3 and the flaps 4 of FIG. 7(f) are arranged so as to bridge the separation portion 10. That is, the female touch fastener F of one flap 4 and the female touch fastener F of the other flap 4 are arranged so as to be apart from each other with the separation portion 10 interposed therebetween.

In this arrangement process, the pair of female touch fasteners F, F of the crotch member 3 are pressed against facing the pair of male touch fasteners M, M of the front panel 1. Therefore, the pair of female touch fasteners F, F engage with the pair of male touch fasteners M, M.

Thus, the crotch member 3 is detachably fixed to the front panel 1 via male and female fasteners. On the other hand, the front panel 1, which is separated by the separation portion 10, is fixed to the crotch member 3 without inadvertently moving in the around-torso direction.

After the arrangement of the crotch member 3 of FIG. 9, the crotch member 3 is folded in two so that the front panel 1 is laid on the back panel 2, the front panel 1 and the back panel 2 are further welded together at the side seal portion 6, and then severed into units of worn articles N.

Next, another embodiment of the structure of the front panel will be described with reference to FIG. 10A and FIG. 10B.

Figures 10A, 10B:
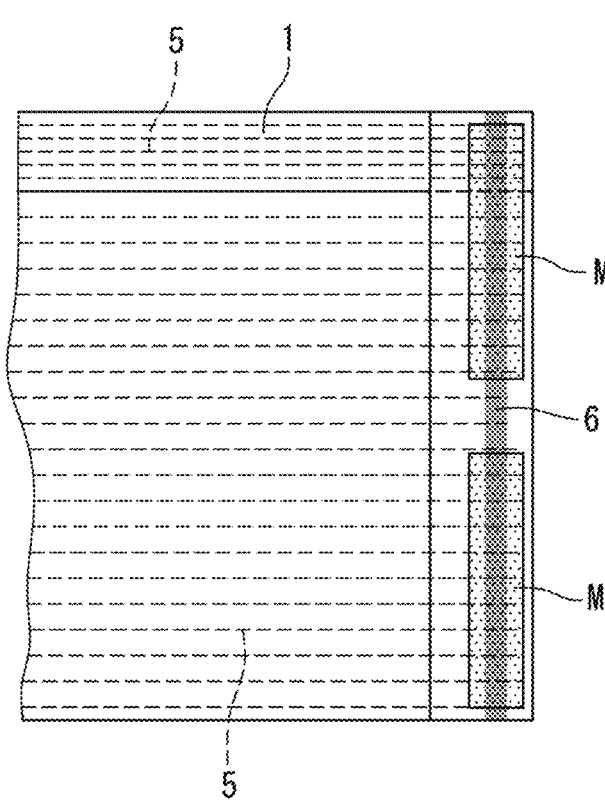

As shown in FIG. 10A and FIG. 10B, a reinforcement strip 1S is provided between the front panel 1 and the male touch fastener M in the separation end portion 1E of the front panel 1 of FIG. 10B close to the separation portion 10 (see FIG. 1A).

This reinforcement strip 1S is provided in an area that is larger than the male touch fastener M, and the male touch fastener M is provided in the area where the reinforcement strip 1S is provided.

The reinforcement strip 1S may include two strips of non-woven fabric layered on each other, for example.

Next, another method for manufacturing a worn article including flaps will be described with reference to FIG. 11.

Figure 7:
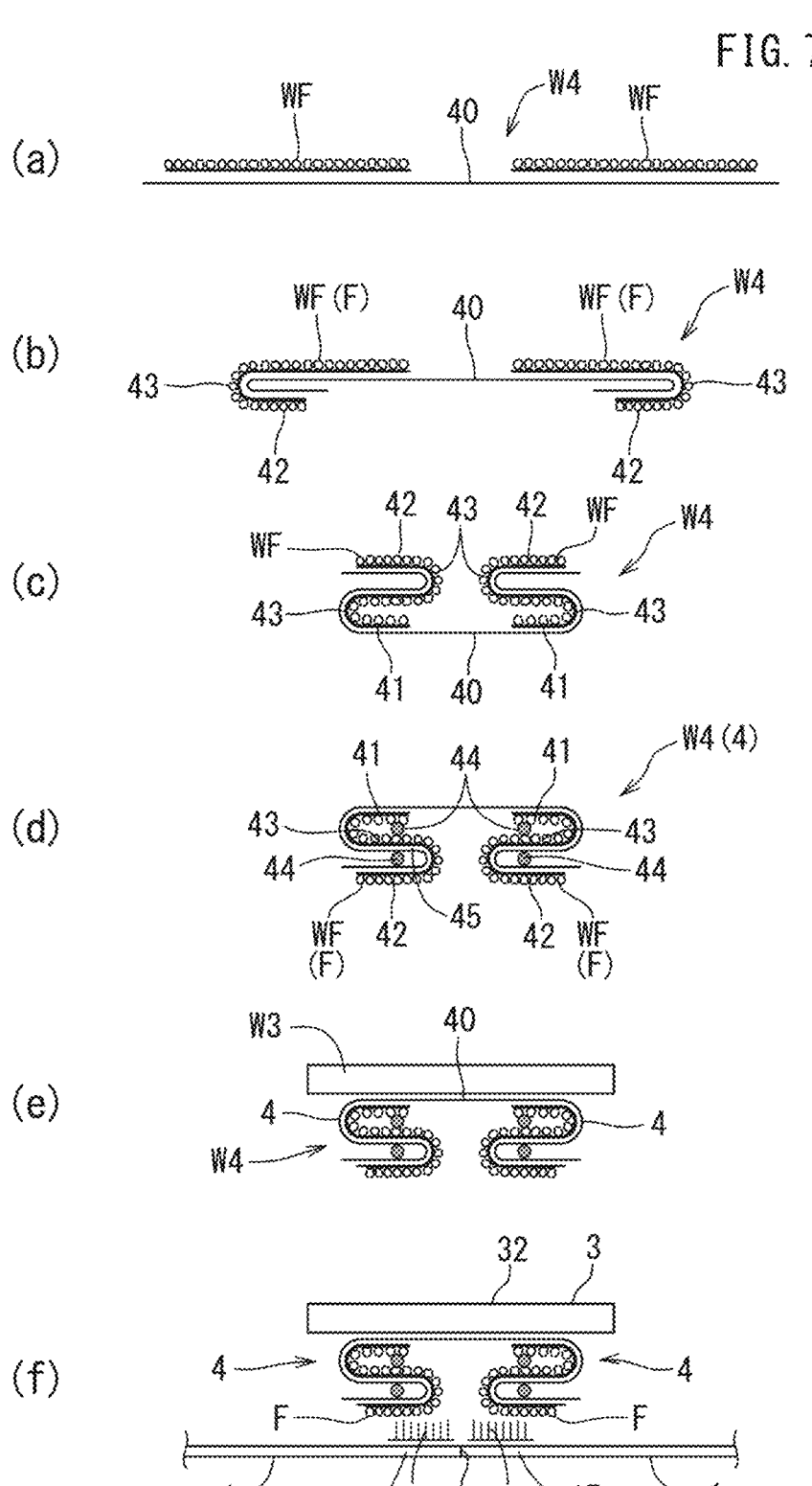
FIG. 7 is a step-by-step view showing a method for manufacturing a worn article including flaps.
Figure 11:
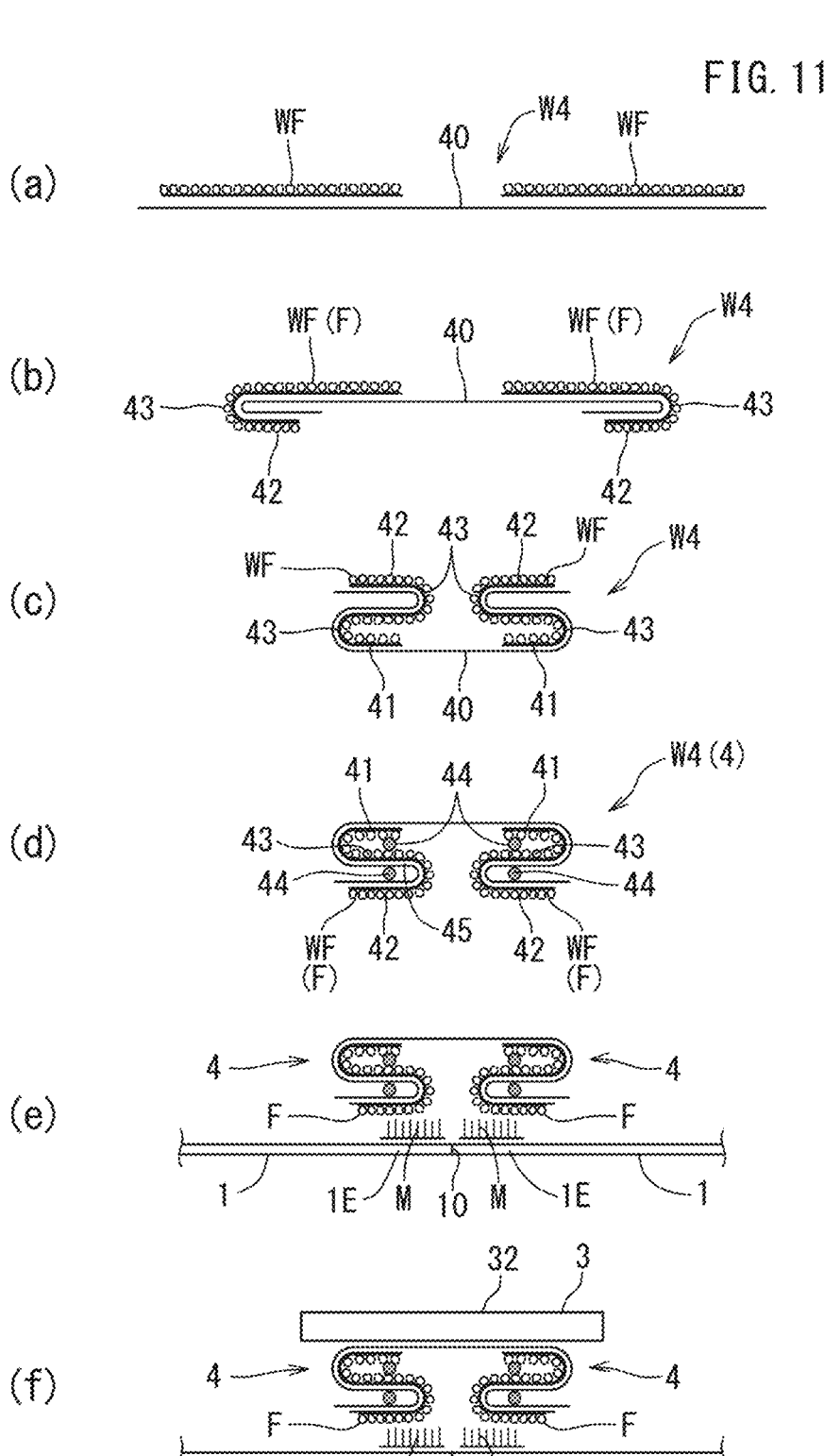
FIG. 11 is a step-by-step view showing another method for manufacturing a worn article including a flap.

In the method for manufacturing a worn article shown in FIG. 11, (a) to (d) are the same as the method shown in FIG. 7, and the manufacturing procedures of (e) and (f) differ from the method shown in FIG. 7.

That is, in FIGS. 7(e) and 7(f), the crotch continuous body W3 is layered on the flap member W4, and then the crotch member 3 is laid on the front panel 1. In contrast, in FIGS. 11(e) and 11(f), the flaps 4 are laid on a precursor member to be the front panel 1 so that the female touch fastener F engages on the male touch fastener M of the front panel 1, and then the crotch member 3 is laid on the flaps 4.

Next, another method for manufacturing the worn article N will be described briefly with reference to FIG. 12.

Figure 12:
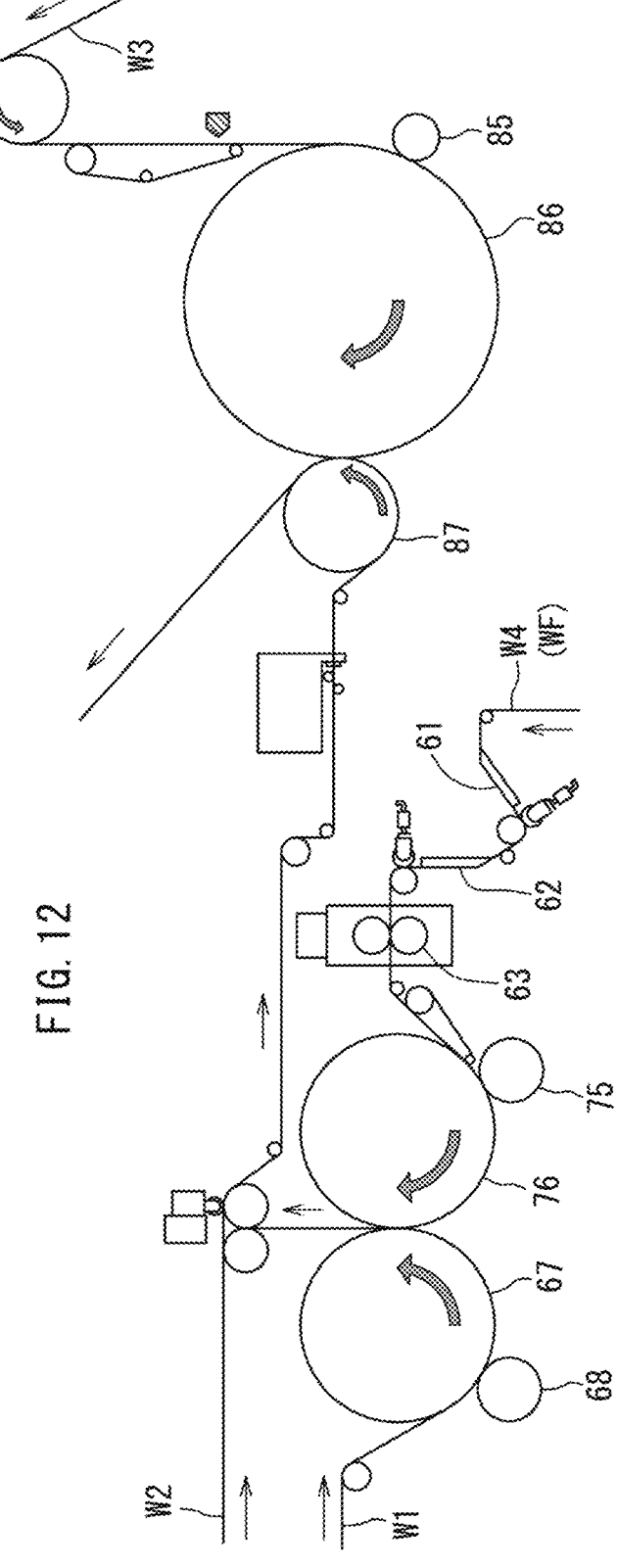
FIG. 12 is a layout diagram showing another example of an equipment for manufacturing the worn article including a flap.

In FIG. 12, after the flap member W4 (FIG. 11(a)) is shaped by the first folder device 61, the second folder device 62 and the welding roll 63, the flap member W4 is cut by a cutter roll 75 into flaps of units of individual worn articles by a cut-and-slip method well known in the art, and then supplied to a re-pitch turn drum 76.

The produced flaps 4 (FIG. 11(e)) are arranged on the front continuous body W1 on the vacuum drum 67. Then, after the front continuous body W1 is attached to the rear continuous body W2, the front continuous body W1 is supplied to a drum 87 of FIG. 12. On the other hand, the crotch member 3 (FIG. 11(f)), which is obtained by severing the crotch continuous body W3 by a cutter 85, is supplied onto a re-pitch turn drum 86, and then attached to the flap 4 on the drum 87 as shown in FIG. 11(f).

Other methods of the present manufacturing method are similar to those shown in FIG. 6 and FIG. 7, and will not be further described below.

Next, technical concepts that can be grasped from the embodiment described above will be described together with their effects.

In a preferred worn article, tentative fastening for maintaining the unused folded state of the flaps 4 is provided on the flaps 4.

In such a case, the folded state of the flaps is maintained until the product reaches consumers.

For example, the tentative fastening may be a bonded portions where materials forming the flaps 4 are bonded by a tentative fastening agent or welded portions where the materials are welded.

Preferably, each female touch fastener F (first touch fastener) is provided so as to extend from the proximal end portion 41 to the protruding end portion 42.

In such a case, the male touch fastener M (second touch fastener) can be fastened at any appropriate position ranging from the proximal end portion 41 to the protruding end portion 42 of the flaps 4, thereby facilitating size adjustment.

More preferably, in the unused state, the flaps 4 are folded in a Z-letter shape having two folded portions 43, and the male touch fastener M engages with the female touch fastener F of the protruding end portion 42.

The flaps 4 folded in a Z-letter shape significantly expand when developed.

Preferably, the crotch member 3 includes the longitudinal portion 30 extending from the crotch portion 31 covering the crotch to the front torso portion 32 covering the front torso of the wearer, and the pair of flaps 4; and the proximal end portions 41 of the pair of flaps 4 are attached to the front torso portion 32, and the protruding end portions 42 protrude in the left-right direction X from the front torso portion 32.

The flaps protruding in the left-right direction X from the front torso portion increase the around-torso size to which adjustment can be made.

In such a case, the pair of flaps 4 include one flap body 40 attached to the front torso portion 32, and the female touch fasteners F, wherein the female touch fasteners F may be provided on the non-skin-contact side 4B of the flap body 40.

Preferably, the reinforcement strip 1S is provided between the front panel 1 and the male touch fastener M in the separation end portion 1E of the front panel 1 that is close to the separation portion 10.

This increases the thickness of the separation end portion 1E and increases the rigidity of the separation end portion 1E, thereby preventing the flap 4 from inadvertently folding to the separation end portion 1E at the time of attachment, and improving the appearance. As the thickness of the separation end portion 1E increases, the rigidity of the separation end portion 1E increases and it is possible to more firmly attach the male touch fastener M to the flap 4.

Preferably, the reinforcement strip 1S is provided in an area larger than the male touch fastener M, and the male touch fastener M is arranged in the area where the reinforcement strip 1S is provided.

Stress localization is likely to occur if the male touch fastener M is attached directly to the front panel 1. However, since the male touch fastener M is arranged in the area of the reinforcement strip is, stress localization is unlikely to occur and it is possible to prevent the flap 4 from inadvertently folding.

A manufacturing method may further include the step of forming the separation portion 10 for each worn article on the front continuous body W1 to be the precursor member.

Preferably, the front continuous body W1 is severed along a virtual cut-off line perpendicular to an around-torso direction at the center in the around-torso direction of the front panel 1, thereby forming the separation portion 10.

With the separation portion 10 obtained by severing the front panel 1 in advance, it is easy to open up the front panel 1 when wearing.

Preferably, the crotch member 3 includes the longitudinal portion 30 extending from the crotch portion 31 covering the crotch to the front torso portion 32 covering the front torso of the wearer, and the pair of flaps 4, wherein the pair of flaps 4 include a pair of female touch fasteners F arranged on one flap body 40 being continuous with each other in the around-torso direction; and the folding step is performed by folding the female touch fastener F together with the flap body 40.

With the female touch fastener F layered on the flap body 40, it is possible to obtain a sufficient rigidity for the flap 4.

Preferably, the crotch member 3 is provided so as to bridge between the precursor member and the rear continuous body W2 in the bridging step while the female touch fastener F is exposed and so that the pair of male touch fasteners M arranged on the precursor member engage with the female touch fastener F.

In such a case, what is obtained by layering together the crotch continuous body W3 and the flap member W4 is cut into units of individual worn articles (the crotch members 3), which are provided so as to bridge between the front panel 1 and the back panel 2, and it can therefore be done with a single re-pitch turn step (re-pitch turn drum), thus enabling reduction in the equipment cost.

Preferably, the engagement step is performed prior to the bridging step, and the crotch member 3 is provided so as to bridge between the flap 4 and the rear continuous body W2 in the bridging step.

In such a case, the female touch fastener F of the flap 4, which is not bonded to the crotch member 3, is fastened to the male touch fastener M. Therefore, members to be fastened together do not include a thick part such as a core, making the fastening easier. This as a result increases the reproducibility of the fastened state and decreases the variations of the fastened state, improving the reliability of the fastening.

Any feature illustrated and/or depicted in conjunction with one embodiment or preferred embodiments may be used in the same or similar form in one or more of the other embodiments, and/or may be used in combination with, or in place of, the other embodiments.

While preferred embodiments have been described above with reference to the drawings, obvious variations and modifications will readily occur to those skilled in the art upon reading the present specification.

For example, the male touch fastener may be provided on the flap, and the female touch fastener on the front panel.

The flap may be continuous with the crotch member.

Thus, such variations and modifications shall fall within the scope of the present invention as defined by the appended claims.

INDUSTRIAL APPLICABILITY

The present invention is applicable to a reclosable pants-type disposable worn article and a method for manufacturing the same.

REFERENCE SIGNS LIST

1: Front panel, 1E: Separation end portion, 1F: Skin-contact side, 1S: Reinforcement strip, 10: Separation portion
2: Back panel
3: Crotch member, 30: Longitudinal portion, 31: Crotch portion, 32: Front torso portion
4: Flap, 4B: Non-skin-contact side, 40: Flap body, 41: Proximal end portion, 42: Protruding end portion, 43: Folded portion, 44: Tentative fastening portion, 45: Middle portion
5: Elastic member
6: Side seal portion, 61: First folder device, 62: Second folder device, 63: Welding roll
64: Cutter roll, 65: Cutter, 66: Re-pitch turn drum, 67: Vacuum drum, 68: Front portion cutter, 75: Cutter roll, 76: Re-pitch turn drum
85: Cutter, 86: Re-pitch turn drum, 87: Drum
F: First touch fastener (female touch fastener), M: Second touch fastener (male touch fastener)
N: Worn article
X: Left-right direction
W1: Front continuous body (an example of precursor member), W2: Rear continuous body, W3: Crotch continuous body, W4: Flap member, WF: Female touch fastener member

The invention claimed is:

1. A reclosable pants-type disposable worn article comprising:
   a front panel and a back panel covering a torso of a wearer;
   a crotch member covering crotch of the wearer and connecting between the front panel and the back panel;
   a separation portion formed on the front panel, thereby making the front panel separated or separable into left and right parts;
   a pair of flaps provided in an area of the crotch member, the pair of flaps opposing the front panel and each extending in a left-right direction from a proximal end portion to a protruding end portion;
   a pair of left and right first touch fasteners,
      the left first touch fastener provided on at least a non-skin-contact side of the protruding end portion of one of the pair of flaps,
      the right first touch fastener provided on at least the non-skin-contact side of the protruding end portion of another one of the pair of flaps; and
   a pair of second touch fasteners provided on a skin-contact side of the front panel and engaging with the pair of first touch fasteners, thereby allowing the front panel to be re-fastened to the crotch member, wherein:
   the separation portion is interposed between the pair of second touch fasteners;
   one of the pair of second touch fasteners is provided on a left side of the separation portion;
   another one of the pair of second touch fasteners is provided on a right side of the separation portion; and
   while in an unused folded state of the worn article, the flaps are engaged with the second touch fasteners in the protruding end portions via the first touch fasteners, and the flaps are folded so that the protruding end portions come closer to the respective proximal end portions; and
   while in a worn state in which the worn article is used, the flaps are capable of being developed so that the first touch fasteners of the protruding end portions are capable of opposing and engaging with the second touch fasteners,
   wherein the first touch fasteners F are each provided extending from the proximal end portion to the protruding end portion, and
   wherein in the unused state, the flaps each are folded in a Z-letter shape having two folded portions, and the second touch fasteners engage with the first touch fasteners of the protruding end portions.

2. The worn article according to claim 1, wherein tentative fastening for maintaining the unused folded state of the flaps is provided on the flaps.

3. The worn article according to claim 2, wherein the tentative fastening is a bonded portion where a material forming the flaps is bonded by a tentative fastening agent or a welded portion where the material is welded.

4. The worn article according to claim 2, wherein:
   the crotch member includes a longitudinal portion extending from a crotch portion covering the crotch to a front torso portion covering a front torso of the wearer, and the pair of flaps; and
   the proximal end portions of the pair of flaps are attached to the front torso portion, and the protruding end portions protrude in the left-right direction from the front torso portion.

5. The worn article according to claim 4, wherein the pair of flaps include one flap body attached to the front torso portion, and the first touch fasteners, wherein the first touch fasteners are provided on the non-skin-contact side of the flap body.

6. The worn article according to claim 1, wherein a reinforcement strip is provided between the front panel and each of the second touch fasteners in a separation end portion of the front panel that is close to the separation portion.

7. The worn article according to claim 6, wherein the reinforcement strip is provided in an area larger than the respective second touch fasteners, and each of the second touch fasteners is arranged within the area where the reinforcement strip is provided.

8. A method for manufacturing a reclosable pants-type disposable worn article, wherein the worn article includes:
  a front panel and a back panel covering a torso of a wearer;
  a crotch member covering crotch of the wearer and connecting between the front panel and the back panel;
  a separation portion formed on the front panel, thereby making the front panel separated or separable into left and right parts;
  a pair of flaps provided in an area of the crotch member, the pair of flaps opposing the front panel and each extending in a left-right direction from a proximal end portion to a protruding end portion;
  a pair of left and right first touch fasteners,
    the left first touch fastener provided on at least a non-skin-contact side of the protruding end portion of one of the pair of flaps,
    the right first touch fastener provided on at least the non-skin-contact side of the protruding end portion of another one of the pair of flaps; and
  a pair of second touch fasteners provided on a skin-contact side of the front panel and engaging with the pair of first touch fasteners, thereby allowing the front panel to be re-fastened to the crotch member, wherein:
  the separation portion is interposed between the pair of second touch fasteners;
  one of the pair of second touch fasteners is provided on a left side of the separation portion;
  another one of the pair of second touch fasteners is provided on a right side of the separation portion; and
  the method for manufacturing the worn article comprises:
  a step of conveying a rear continuous body to be the back panel in such a manner that an around-torso direction is a conveyance direction;
  a step of conveying a precursor member to be the front panel in such a manner that an around-torso direction is the conveyance direction;
  a bridging step of providing the crotch member so as to bridge between the rear continuous body and the precursor member being conveyed;
  a step of, prior to the bridging step, folding a flap member to be the flaps so that the protruding end portions of the pair of flaps come closer to the respective proximal end portions and so that the first touch fasteners are exposed in the protruding end portions; and
  an engagement step of, while the first touch fasteners are exposed, engaging the pair of second touch fasteners arranged on the precursor member with the first touch fasteners.

9. The manufacturing method according to claim 8, further comprising the step of forming the separation portion for each worn article on a front continuous body to be the precursor member.

10. The manufacturing method according to claim 9, wherein the separation portion is formed by severing the front continuous body along a virtual cut-off line perpendicular to the around-torso direction at a center in the around-torso direction of an area corresponding to the front panel.

11. The manufacturing method according to claim 8, wherein:
  the crotch member includes a longitudinal portion extending from a crotch portion covering the crotch to a front torso portion covering a front torso of the wearer, and the pair of flaps,
  wherein the pair of flaps include the pair of first touch fasteners arranged on one flap body being continuous with the flaps in the around-torso direction; and
  the folding step is performed by folding the first touch fasteners together with the flap body.

12. The manufacturing method according to claim 8, wherein the crotch member is provided so as to bridge between the precursor member and the rear continuous body in the bridging step while the first touch fasteners are exposed and so that the pair of second touch fasteners arranged on the precursor member engage with the first touch fasteners.

13. The manufacturing method according to claim 8, wherein the engagement step is performed prior to the bridging step, and
  the crotch member is provided so as to bridge between the corresponding flap and the rear continuous body in the bridging step.

14. A reclosable pants-type disposable worn article comprising:
  a front panel and a back panel covering a torso of a wearer;
  a crotch member covering crotch of the wearer and connecting between the front panel and the back panel;
  a separation portion formed on the front panel, thereby making the front panel separated or separable into left and right parts;
  a pair of flaps provided in an area of the crotch member, the pair of flaps opposing the front panel and each extending in a left-right direction from a proximal end portion to a protruding end portion;
  a pair of left and right first touch fasteners,
    the left first touch fastener provided on at least a non-skin-contact side of the protruding end portion of one of the pair of flaps,
    the right first touch fastener provided on at least the non-skin-contact side of the protruding end portion of another one of the pair of flaps; and
  a pair of second touch fasteners provided on a skin-contact side of the front panel and engaging with the pair of first touch fasteners, thereby allowing the front panel to be re-fastened to the crotch member, wherein:
  the separation portion is interposed between the pair of second touch fasteners;
  one of the pair of second touch fasteners is provided on a left side of the separation portion;
  another one of the pair of second touch fasteners is provided on a right side of the separation portion; and
  while in an unused folded state of the worn article, the flaps are engaged with the second touch fasteners in the protruding end portions via the first touch fasteners, and the flaps are folded so that the protruding end portions come closer to the respective proximal end portions; and while in a worn state in which the worn article is used, the
flaps are capable of being developed so that the first
touch fasteners of the protruding end portions are
capable of opposing and engaging with the second
touch fasteners, wherein tentative fastening for maintaining the unused
folded state of the flaps is provided on the flaps, wherein:

the crotch member includes a longitudinal portion extend-
ing from a crotch portion covering the crotch to a front
torso portion covering a front torso of the wearer, and
the pair of flaps; and the proximal end portions of the pair of flaps are attached
to the front torso portion, and the protruding end
portions protrude in the left-right direction from the
front torso portion.

15. The reclosable pants-type disposable worn article
according to claim 14, wherein the pair of flaps includes one
flap body attached to the front torso portion, and the first
touch fasteners, wherein the first touch fasteners are pro-
vided on the non-skin-contact side of the flap body.

\* \* \* \* \*